United States Patent

Keller

Patent Number: 5,383,933
Date of Patent: Jan. 24, 1995

[54] ENDOPROSTHESIS

[75] Inventor: Arnold Keller, Kayhude, Germany

[73] Assignee: Waldemar Link GmbH & Co., Hamburg, Germany

[21] Appl. No.: 94,082

[22] PCT Filed: Nov. 26, 1992

[86] PCT No.: PCT/EP92/02730
  § 371 Date: Jul. 27, 1993
  § 102(e) Date: Jul. 27, 1993

[87] PCT Pub. No.: WO93/10724
  PCT Pub. Date: Jun. 10, 1993

[30] Foreign Application Priority Data

Dec. 2, 1991 [DE] Germany .................. 9114970

[51] Int. Cl.⁶ .................................. A61F 2/38
[52] U.S. Cl. .................................. 623/16; 623/18
[58] Field of Search .................. 623/16, 18, 11, 66

[56] References Cited

U.S. PATENT DOCUMENTS

| | | | |
|---|---|---|---|
| 4,578,081 | 3/1986 | Harder | 623/22 |
| 4,938,768 | 7/1990 | Wu | 623/16 |
| 5,129,898 | 7/1992 | Brusasco | 623/16 X |

FOREIGN PATENT DOCUMENTS

| | | | |
|---|---|---|---|
| 0290767 | 11/1988 | European Pat. Off. | 623/16 |
| 3909182 | 8/1990 | Germany | 623/11 |
| 1671286 | 8/1991 | U.S.S.R. | 623/16 |

*Primary Examiner*—David Isabella
*Attorney, Agent, or Firm*—Chilton, Alix & Van Kirk

[57] ABSTRACT

Endoprosthesis having two prosthesis parts which are connected by mutually overlapping lugs. The safety of the connection is increased due to the fact that the ends (5) of the lug clamp (3) are received in a positive-locking manner by pocket clamps (9) on the respective other prosthesis part. The engagement position of the lugs (3) is secured by screws (7). The contact surface (6) with which the lugs (3) face one another, runs at an inclination to the longitudinal axis of the connection region (2) of the prosthesis, which, on the one hand, allows the thickening of the lugs (3) near to their transition into the associated prosthesis part and a good power transition and, on the other hand, permits a clearance-free engagement of the ends (5) of the overlapping parts (3) with the pocket clamps (9) in the engagement position.

8 Claims, 1 Drawing Sheet

ENDOPROSTHESIS

The invention relates to an endoprosthesis having two prosthesis parts which are connected by an overlapping connection.

The problem frequently exists of connecting two prosthesis parts rigidly to one another after they have been implanted separately. An example of this is a prosthesis for the rigid connection of two bone fragments or for the arthrodesis of two tubular bones which are otherwise connected by a joint. At the site of the fracture or joint, the two bones can be angled towards one another so that the shafts of the two prostheses can be inserted in the bones. The bones are then aligned relative to one another and the parts of the prostheses facing one another are connected to one another. This can be done, for example, in a positive-locking manner using a cone or pin at the end of one shaft which is inserted in a corresponding sleeve at the end of the other shaft. However, this has the disadvantage that, for inserting the cone or pin in the associated sleeve, the two bones must firstly be distracted by the length of the cone or pin, which can be difficult or harmful. A connection is therefore desired which can be closed without substantial distraction. For this purpose, the lug connection is available, in which two lugs, provided at the ends of the prosthesis shafts, are screwed to one another, which has the disadvantage, however, that the reliability of the connection depends on the screws which may become loose, and that the transition from the lugs to the shafts forms a weak point.

The invention avoids these disadvantages in a lug connection due to the fact that the ends of the mutually overlapping lugs are received in a positive-locking manner by pockets on the respective other prosthesis part. In order to couple the lugs to one another, only a small distraction is required, whose length corresponds to the length of the engagement of the lug ends in the associated pockets. This length is far shorter than in a pin or cone connection, in which distraction is required over virtually the entire length of the connection region.

According to the invention, an engagement length of the lug ends in the associated pockets of no more than 1/5, preferably no more than 1/10, of the overall overlapping length, is sufficient.

Devices for securing the lugs in the engagement position are expediently provided, which merely need to ensure that no longitudinal displacement of the lugs relative to one another can take place, by means of which the lug ends could come out of the associated pockets. The pertinent technology provides various types of such means. The simplest method is to screw the lugs to one another. It is notable in this case that the screw connection prevents longitudinal displacement even if a screw may have loosened slightly. In contrast to the known screwed lug connections, the safety of the connection is therefore not impaired by screws becoming loose.

According to a further feature of the invention, the lugs are thicker near to their transition into the associated prosthesis part than at their free end, in that the contact surface with which they face one another runs at an inclination to the common longitudinal axis of the connection region of the prosthesis parts. Due to the fact that the lugs are thickest at that end at which they are firmly connected to the associated prosthesis part, they can merge into the prosthesis part with equal cross-section without forming dangerous notches, while their end which engages in the pocket of the other prosthesis part is correspondingly thinner. The taper allows the lug ends and the pockets surrounding them to become wedged in one another, thus resulting in a self-locking, clearance-free engagement position.

The invention is explained in greater detail below with reference to the drawing which shows an advantageous exemplary embodiment of a prosthesis or rail for the arthrodesis of the knee joint.

Figure 1:
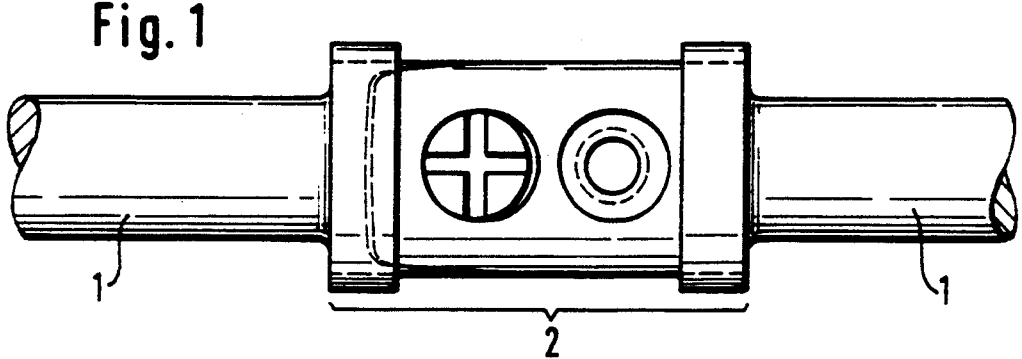
FIG. 1 shows a lateral view of the connection region of the prosthesis.
Figure 2:
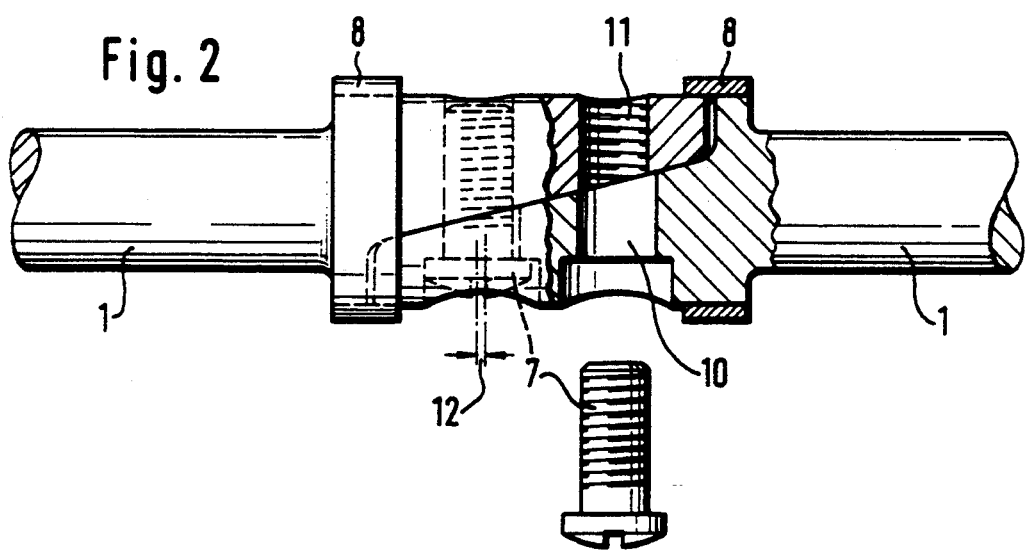
FIG. 2 shows a lateral view transversely to that according to FIG. 1.
Figure 3:
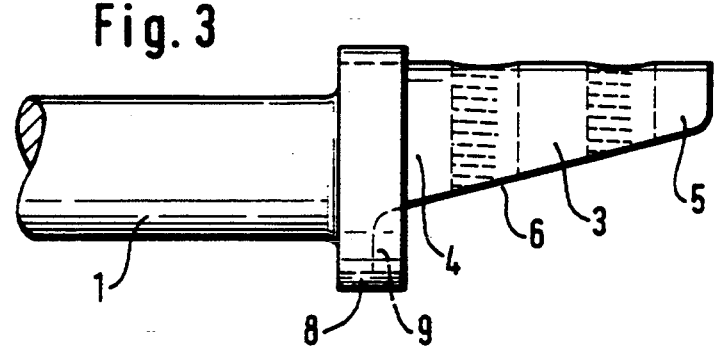
FIGS. 3 and 4 show special lateral views of the connection regions of the two prosthesis parts.
Figure 4:
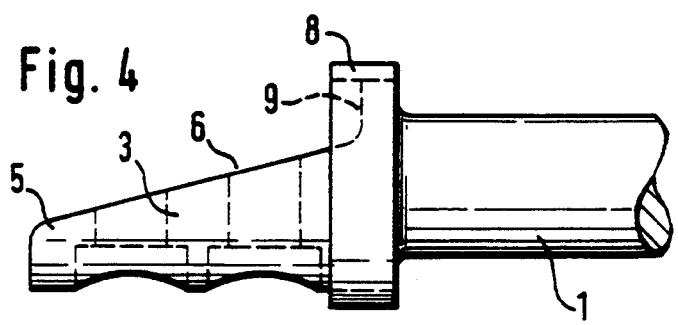

The two prosthesis parts each have a shaft 1 for implantation in the femur or tibia. Their connection region 2 comprises two lugs 3 which complement one another to form a cylindrical contour and whose contact surface 6 runs at such an inclination that in each case the thicker end 4 merges integrally and with undiminished bending strength into the associated shaft part 1, while the free end 5 in the plane of illustration of FIGS. 3 and 4 is approximately half as thick as the thicker end 4 and its cross-sectional area is about ⅓ as large. The lugs lie flatly against one another along the surface 6 in the connected state according to FIGS. 1 and 2. They can be secured in this position by means of screws 7.

Figure 5:
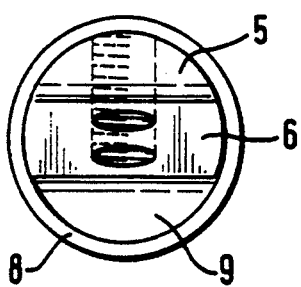
FIGS. 5 and 6 show longitudinal views of the connection regions of the prosthesis parts.
Figure 6:
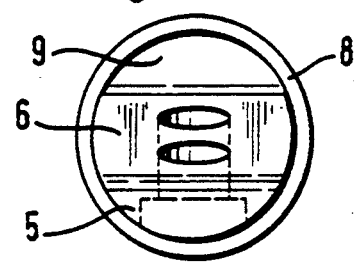

At the root of each lug 3, the latter is surrounded by a ring 8 which, with the associated end of the contact surface 6, encloses a pocket 9 whose cross-section in the longitudinal view according to FIGS. 5 and 6 corresponds to that of the end part 5 of the respective other lug. In this case, the dimensions are selected such that, in the clearance-free, fitted-together state which is illustrated in FIG. 3, the contact surfaces 6 and the circumferential surfaces of the lug ends 5 come into clearance-free contact with one another and with the respective ring 8 thus guaranteeing a rigid connection solely by the interaction of the lug ends 5 with the pockets 9. In this case, the safety of the connection is further increased by the wedge effect of the contact surface 6 under the load of the prosthesis which attempts to push the two prosthesis parts together. In the engagement position, the lugs are secured by screws 7, the associated, opposite screw holes 10, 11 being arranged in such a way that, even if they are slightly offset relative to one another in the assembled state, such as is indicated at 12, the complete engagement of the lug ends 5 in the pockets 9 is still guaranteed. The ring 8 is preferably attached firmly to the associated prosthesis part.

When using screws to secure the engagement, these can be used for transmitting force and can be dimensioned accordingly.

I claim:

1. An implantable biocompatible endoprosthesis sized and shaped for attachment to bones in a human body comprising two prosthesis parts, said parts including mutually overlapping elongated connecting lugs of predetermined length, characterised in that each of the lugs (3) includes a free end portion (5) and a peripherally lipped pocket (9) whereby upon overlapping assembly said lugs the free end portion of each lug is received in a positive-locking manner by the lipped pocket on the respective other prosthesis.

2. Endoprosthesis according to claim 1, characterised in that the pockets (9) have a length of no more than 1/5 of the overall lug length.

3. Endoprosthesis according to claim 1, characterised in that the lugs (3) are fitted with devices for securing the overlapping lugs in an assembled position.

4. Endoprosthesis according to claim 3, characterised in that the devices for securing in an assembled position are formed by at least one screw (7).

5. Endoprosthesis according to one of claim 1, characterised in that the lugs (3) are thicker at the end opposite their free end than at their free end.

6. Endoprosthesis according to claim 5, characterised in that the overlapping lugs (3) define a connection region (2) of the prosthesis and each lug includes a complementary confronting contact surface (6) extending at an inclination to a longitudinal axis of the connection region (2) of the prosthesis.

7. Endoprosthesis according to claim 5, characterised in that each lug is tapered toward its free end to impart a wedge configuration and the free ends (5) of the overlapping lugs (3) and the pockets (9) interfit in a clearance-free complementary manner in an assembled position due to the wedge configuration.

8. Endoprosthesis of claim 2 wherein the length of the pockets is no more than 1/10 of the overall lug length.

* * * * *